(12) United States Patent
Wang et al.

(10) Patent No.: US 11,408,781 B2
(45) Date of Patent: Aug. 9, 2022

(54) THERMAL SENSOR PACKAGE FOR EARBUDS

(71) Applicant: ORIENTAL SYSTEM TECHNOLOGY INC., Hsinchu (TW)

(72) Inventors: Chein-Hsun Wang, Hsin-Chu (TW); Ming Le, New Taipei (TW); Yu-Chih Liang, Hsinchu (TW); Tung Yang Lee, Zhubei (TW); Chih-Yung Tsai, Taichung (TW)

(73) Assignee: ORIENTAL SYSTEM TECHNOLOGY INC., Hsinchu (TW)

( * ) Notice: Subject to any disclaimer, the term of this patent is extended or adjusted under 35 U.S.C. 154(b) by 693 days.

(21) Appl. No.: 16/441,916

(22) Filed: Jun. 14, 2019

(65) Prior Publication Data

US 2020/0249101 A1  Aug. 6, 2020

(30) Foreign Application Priority Data

Jan. 31, 2019 (CN) .......................... 201910098050.0

(51) Int. Cl.
*A61B 5/01* (2006.01)
*G01K 13/20* (2021.01)
*A61B 5/00* (2006.01)
*H04R 1/10* (2006.01)

(52) U.S. Cl.
CPC .............. *G01K 13/223* (2021.01); *A61B 5/01* (2013.01); *A61B 5/6803* (2013.01); *H04R 1/1016* (2013.01); *H04R 1/1058* (2013.01); *A61B 5/6817* (2013.01); *A61B 2560/0252* (2013.01); *A61B 2562/185* (2013.01); *H04R 2420/07* (2013.01)

(58) Field of Classification Search
CPC ........ G01K 13/223; A61B 5/01; A61B 5/6803
See application file for complete search history.

(56) References Cited

U.S. PATENT DOCUMENTS

| 10,096,724 B2 | 10/2018 | Van Buggenhout et al. | |
|---|---|---|---|
| 2016/0153836 A1* | 6/2016 | Ishihara | A61B 5/6898 250/338.1 |
| 2017/0035344 A1* | 2/2017 | Tzvieli | A61B 5/015 |
| 2019/0117155 A1* | 4/2019 | Cross | A61B 5/6817 |

* cited by examiner

*Primary Examiner* — Suhan Ni
(74) *Attorney, Agent, or Firm* — Muncy, Geissler, Olds & Lowe, P.C.

(57) ABSTRACT

A thermal sensor package for earbuds includes two thermopile sensor elements on a single thermopile sensor chip, and the two thermopile sensor elements are separated by a block wall of a cap. One of the thermopile sensor elements senses external infrared thermal radiation through a window of the cap, and the other thermopile sensor element senses internal infrared thermal radiation from a package structure as a basis for correcting compensation. Therefore, the foregoing thermal sensor package for earbuds can quickly correct a measurement error caused by the package structure to improve the measurement accuracy. In addition, the forgoing thermal sensor package for earbuds has a simple packaging step and is easy to arrange a silicon based infrared lens to expand its application.

17 Claims, 4 Drawing Sheets

THERMAL SENSOR PACKAGE FOR EARBUDS

BACKGROUND OF THE INVENTION

1. Field of the Invention

The present invention relates to a thermal sensor package, and more particularly to a thermal sensor package for earbuds.

2. Description of the Related Art

The popularity of wireless earbuds for mobile phone leads to the demand of more features for sport fans, such as heart rate and temperature measurement etc. Traditional ear thermometer adopts thermopile sensor to measure our core temperature in a noncontact manner. Nevertheless the ear thermometer with the thermopile sensor faces some constraints, for example, the device must be stable enough or it only measure at once to maintain required accuracy. For long time temperature measurement with insertion in ear canal, we still face the problem of thermal contamination. This is due to the thermopile sensor receives radiation energy from eardrum as well as thermal gradient radiation from a cap of thermopile sensor package. Therefore, for long term insertion in the ear canal, the cap of the thermopile sensor will be heated up and the temperature gradient of the cap to cold junction of the thermopile sensor will create an error in temperature measurement.

For example, refer to FIG. 7, a thermopile sensor 700 receives target heat source radiation IR1, and cap radiation IR2 and IR3 due to thermal gradient between a cap 703 and cold junction 702 of the thermopile sensor. The cap radiation came from environmental heat source 800 (such as ear canal) to the cap 703 through radiation or contact that heat up the cap 703, and there is thermal resistance θ1 between the cap 703 to sensor base 701 and thermal resistance θ2 between sensor base 701 to cold junction 702 that the temperature gradient generates thermal radiation of the cap 703. The cap radiation IR2 and IR3 will create error in temperature measurement of the thermopile sensor 700.

In order to minimize the cap effect, a traditional thermopile sensor used in an ear thermometer or industrial remote temperature measurement is packaged in a metal cap package and then arranges a big heat sink on metal cap package to minimize temperature fluctuation of the cap. Nevertheless, this type package for thermopile sensor cannot provide accurate temperature measurement for ambient temperature fluctuation or extreme temperature environment such as high temperature environment. Meanwhile this type of package is not miniature for earbuds to fit in ear canal.

In another traditional thermal sensor, we might use one dummy thermopile sensor that has the same geometry of an active thermopile sensor. The dummy thermopile sensor has a window that is blocked for target heat source radiation IR1, therefore it only senses the cap radiation such as IR2 and IR3. And then the actual sensed signal output from the active thermopile sensor is deducted from the output of dummy thermopile sensor.

In prior art approaches to implement the dummy thermopile sensor with the active thermopile sensor in the same metal package is to use an block wall on the base package between the dummy and active thermopile sensors, which is costly in base package and there is some crosstalk due to a gap between the window of the cap and the block wall.

Another approach to implement dummy thermopile sensor was disclosed in U.S. Pat. No. 10,096,724 B2 that used a silicon based cap to cover the active and dummy thermopile sensors except that the window of dummy thermopile sensor was blocked by metal coating. After the cap is attached to a sensor integrated IC, wire bonding is applied and then a molding process is required to encapsulate the whole sensor IC, which needs the costly tooling and higher manufacture cost.

Accordingly, it will be appreciated that a need presently exists for thermopile sensors package which is miniature, cost effective, ease of manufacture and high accuracy in temperature measurement, that can overcome thermal contamination of cap thermal gradient effect and it is suitable for long term operation within the ear canal for body temperature measurement.

SUMMARY OF THE INVENTION

The present invention is directed to a thermal sensor package for earbuds, which encapsulates a thermopile sensor chip including a first and a second thermopile sensor elements between a package substrate and a cap so that the thermal sensor package for earbuds of the present invention is miniature, cost effective, ease of manufacture and high accuracy in temperature measurement for long term operation within the ear canal for body temperature measurement.

In one embodiment, the proposed thermal sensor package for earbuds includes a package substrate, a thermopile sensor chip, a cap and a silicon based infrared lens. The thermopile sensor chip is mounted on the package substrate and electrically connected with the package substrate. The thermopile sensor chip includes a first thermopile sensor element, a second thermopile sensor element, a silicon based temperature sensor and a signal processor. The first thermopile sensor element is configured for receiving external infrared thermal radiation to generate a first sensing signal. The second thermopile sensor element is configured for receiving internal infrared thermal radiation to generate a second sensing signal. The silicon based temperature sensor is configured for sensing ambient temperature to generate an ambient temperature signal. The signal processor is electrically connected with the first thermopile sensor element, the second thermopile sensor element and the silicon based temperature sensor for processing the first sensing signal, the second sensing signal and the ambient temperature signal to output a sensing temperature of the thermopile sensor chip. The cap is arranged on the package substrate to define an accommodation space with the package substrate to accommodate the thermopile sensor chip. The cap includes a first window, a shielding portion and a block wall, wherein the first window is arranged corresponding to the first thermopile sensor element, the shielding portion is arranged corresponding to the second thermopile sensor element so that the second thermopile sensor element receives the internal infrared thermal radiation from the shielding portion, and the block wall is arranged between the first thermopile sensor element and the second thermopile sensor element. The silicon based infrared lens is arranged at the first window of the cap to limit a field of view of the first thermopile sensor element.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENT

The detailed explanation of the present invention is described as follows. The described preferred embodiments are presented for purposes of illustrations and description, and they are not intended to limit the scope of the present invention.

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

A thermal sensor package of the present invention is applied to earbuds which is inserted into an ear canal of user during use. It should be noted that earbuds is also known as canalphones. To simplify the description, the term "earbuds" is used herein to refer to earbuds and canalphones.

Figure 1:
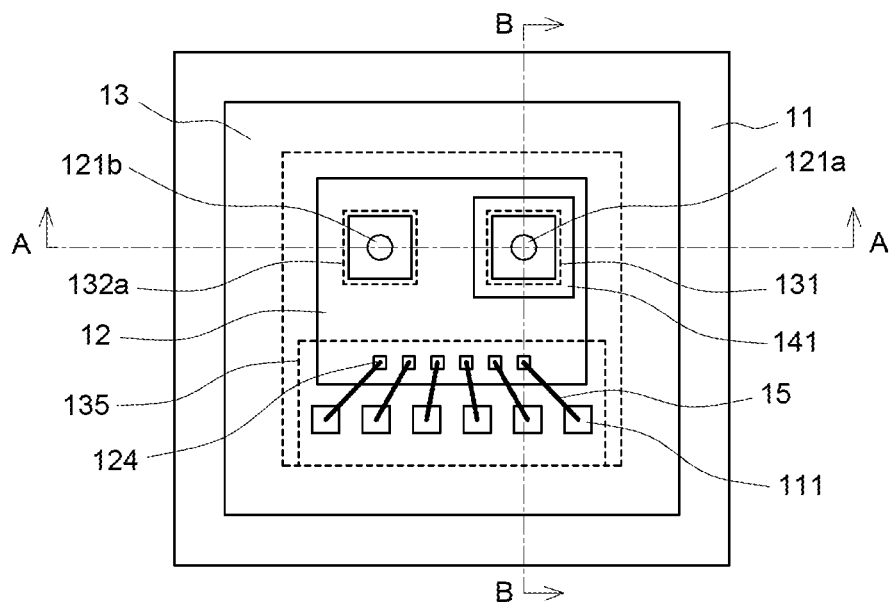
FIG. 1 is a diagram schematically illustrating a thermal sensor package for earbuds according to a first embodiment of the present invention.
Figure 2:
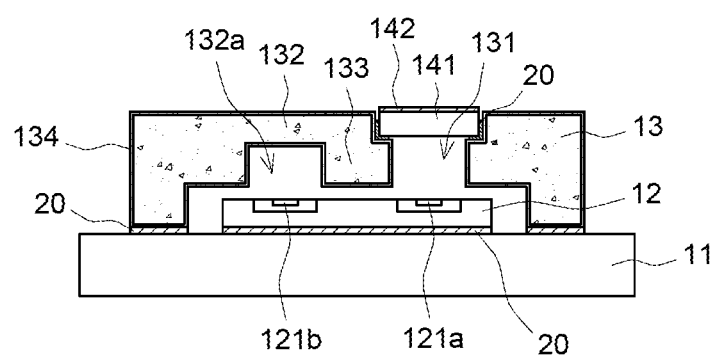
FIG. 2 is a cross-sectional diagram schematically illustrating the thermal sensor package for earbuds according to the first embodiment of the present invention taken along line AA of FIG. 1.
Figure 3:
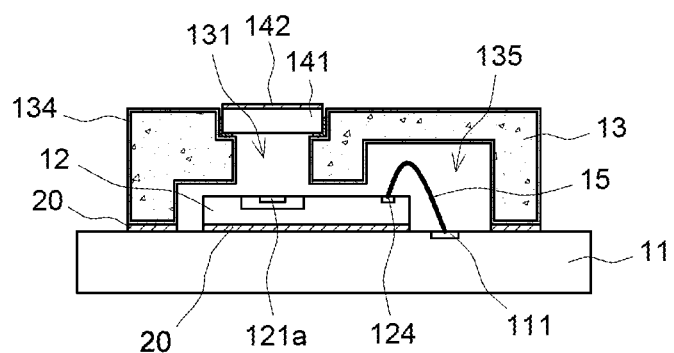
FIG. 3 is a cross-sectional diagram schematically illustrating the thermal sensor package for earbuds according to the first embodiment of the present invention taken along line BB of FIG. 1.

Referring to FIG. 1 to FIG. 3, a thermal sensor package for earbuds according to an embodiment of the present invention includes a package substrate 11, a thermopile sensor chip 12, a cap 13 and a silicon based infrared lens 141. A material of the package substrate 11 may be bismaleimide triazine (BT) resin or ceramic material. It can be understood that the package substrate 11 includes a plurality of conductive contacts and conductive traces electrically connected with the corresponding conductive contacts for electrically connecting the thermocouple sensor chip 12 and the package substrate 11 and outputting sensing signals generated by the thermopile sensor chip 12 to an exterior. The detailed structure of the package substrate 11 is well known to those skilled in the art, and therefore will not be described herein.

The thermopile sensor chip 12 is mounted on the package substrate 11 and electrically connected with the package substrate 11. For example, referring to FIG. 3, the thermopile sensor chip 12 can be electrically connected to the conductive contacts 111 on the package substrate 11 through the conductive contacts 124 on the thermopile sensor chip 12 and the leads 15. In one embodiment, the thermopile sensor chip 12 is attached to the package substrate 11 with thermal conductive adhesive 20. The thermal conductive adhesive 20 can reduce the thermal resistance between the package substrate 11 and the thermopile sensor chip 12, which facilitates the thermopile sensor chip 12 to sense ambient temperature.

In one embodiment, the thermopile sensor chip 12 may be an integrated chip. For example, the thermopile sensor chip 12 includes a first thermopile sensor element 121a, a second thermopile sensor element 121b, a silicon based temperature sensor 122 (shown in FIG. 4) and a signal processor 123 (shown in FIG. 4). The first thermopile sensor element 121a is configured for receiving external infrared thermal radiation to generate a first sensing signal. The second thermopile sensor element 121b is configured for receiving internal infrared thermal radiation to generate a second sensing signal. The silicon based temperature sensor 122 is configured for sensing ambient temperature to generate an ambient temperature signal. The signal processor 123 is electrically connected with the first thermopile sensor element 121a, the second thermopile sensor element 121b and the silicon based temperature sensor 122 and processes the first sensing signal, the second sensing signal and the ambient temperature signal output by the first and second thermopile sensor element 121a, 121b and the silicon based temperature sensor 122 to output a sensing temperature of the thermopile sensor chip 12.

The cap 13 is arranged on the package substrate 11 and defines an accommodation space with the package substrate 11 so that the thermopile sensor chip 12 can be disposed in the accommodation space between the cap 13 and the package substrate 11. In on embodiment, the cap 13 is attached to the package substrate 11 with thermal conductive adhesive 20. The thermal conductive adhesive 20 can reduce the thermal resistance between the cap 13 and the package substrate 11 so as to make the temperature of the package substrate 11 easy to change with the ambient temperature. Referring to FIG. 2, the cap 13 includes a first window 131, a shielding portion 132 and a block wall 133. The first window 131 is arranged corresponding to the first thermopile sensor element 121a, so that the first thermopile sensor element 121a receives external infrared thermal radiation, such as the infrared thermal radiation from the object to be tested, through the first window 131. In the embodiment shown in FIG. 2, the first window 131 is a through hole, and the sidewall of the through hole is perpendicular to the package substrate 11, but is not limited thereto.

The shielding portion 132 is arranged corresponding to the second thermopile sensor element 121b, so that the second thermopile sensor element 121b merely receives the internal infrared thermal radiation from the shielding portion 132. The block wall 133 is arranged between the first thermopile sensor element 121a and the second thermopile sensor element 121b. The block wall 133 can block infrared thermal radiation to prevent the first thermopile sensor element 121a from receiving the internal infrared thermal radiation radiated by the shielding portion 132 and prevent the second thermopile sensor element 121b from receiving the external infrared thermal radiation radiated by the object to be tested. In one embodiment, the cap 13 may be a material that is not transparent to infrared rays, such as liquid crystal polymer (LCP). The advantage of cap 13 as LCP is that the thermal sensor of the present invention can pass through the high temperature process of the lead-free reflow oven during SMD process, that is, it does not melt or collapse, and the performance of the chip will not deteriorate.

The silicon based infrared lens 141 is arranged at one end of the first window 131 of the cap 13 to limit a field of view of the first thermopile sensor element 121a. For example, the field of view of the first thermopile sensor element 121a is less than 30 degrees. In one embodiment, the silicon based infrared lens 141 is arranged at the first window 131 of the cap 13 with thermal conductive adhesive 20. The thermal conductive adhesive 20 can reduce the thermal resistance between the cap 13 and the silicon based infrared lens 141 so as to make the temperature gradient between the silicon based infrared lens 141 and the cap 13 is minimized. In one embodiment, the silicon based infrared lens 141 is coated with a filter 142. The filter 142 can select the infrared thermal radiation pass of a specific band.

Referring to FIG. 2 again, in one embodiment, the cap 3 is coated with a metallic layer 134 on an inner surface and an outer surface. The metallic layer 134 includes at least one of copper, aluminum, nickel, chrome and stainless steel. As previously mentioned, the material of the cap 13 may be a LCP which is easily injection molded and the metallic layer 134 can be formed on the inner and outer surfaces of the cap 13 by sputtering or electro-plating process. The metallic layer 134 on the outer surface of the cap 13 can block thermal radiation from other heat sources in the external environment. Further, the metallic layer 134 on the outer and inner surfaces of the cap 13 are connected with each other, and the heat conduction effect of the metallic layer 134 allows the inner and outer sides of the cap 13 to reach a uniform temperature faster. The metallic layer 134 on the inner surface of the cap 13 can reduce the emissivity of the cap 13 and increase the blocking infrared effect of the block wall 133. In one embodiment, the width of the block wall 133 is greater than or equal to 0.1 mm. For example, the width of the block wall 133 is 0.2 mm. In one embodiment, a distance between the block wall 133 of the cap 13 and the thermopile sensor chip 12 is equal to or less than 100 μm. For example, the distance between the block wall 133 of the cap 13 and the thermopile sensor chip 12 is 25 μm to 75 μm. In a preferred embodiment, the distance between the block wall 133 of the cap 13 and the thermopile sensor chip 12 is 50 μm to 75 μm.

Referring to FIG. 2 again, in order to reduce the heat conduction between the shielding portion 132 and the second thermopile sensor element 121b caused by the air disturbance, in one embodiment, a distance between the shielding portion 132 and the second thermopile sensor element 121b is greater than or equal to 100 μm. In a preferred embodiment, the distance between the shielding portion 132 and the second thermopile sensor element 121b is between 200 μm and 500 μm. For example, a cavity 132a may be formed between the shielding portion 132 and the second thermopile sensor element 121b to control the distance from the shielding portion 132 to the second thermopile sensor element 121b. It can be understood that, referring to FIG. 3, a cavity 135 can be formed at a position of the cap 13 corresponding to the wire-bonding area to accommodate the wire 15. In one embodiment, a distance from the inner side of the cavity 135 to the thermopile sensor chip 12 is greater than or equal to 200 μm.

Figure 4:
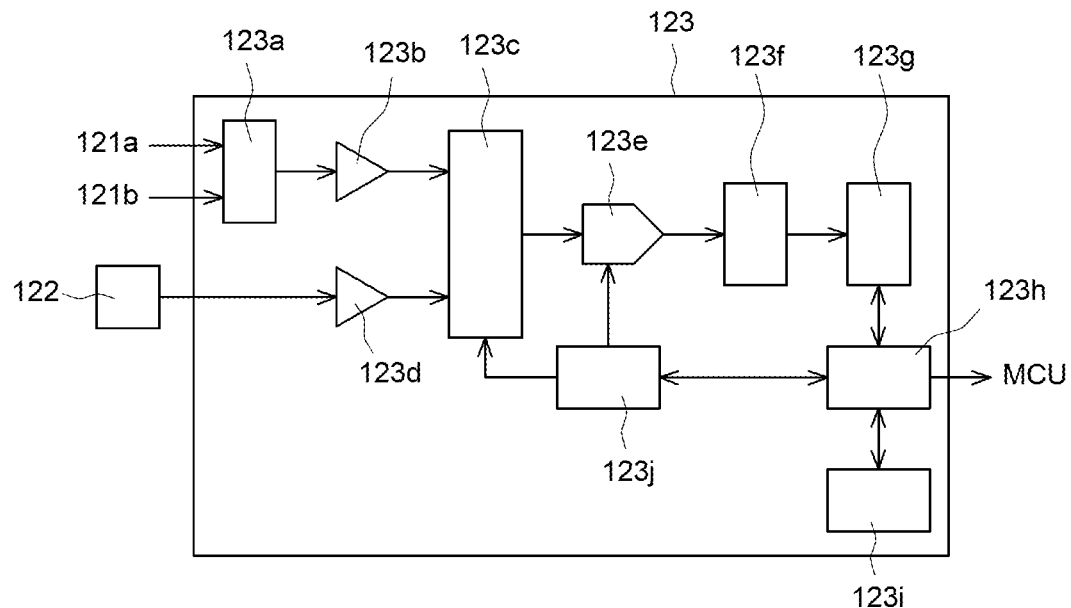
FIG. 4 is a block diagram schematically illustrating a signal processor of a thermal sensor package for earbuds according to an embodiment of the present invention.

Referring to FIG. 4, in one embodiment, the signal processor 123 includes multiplexers 123a and 123c, a programmable gain amplifier 123b, a buffer amplifier 123d, an analog to digital converter 123e, a digital filter 123f, a register 123g, and an I²C (Inter-Integrated Circuit) communication interface 123h, a non-volatile memory 123i and a program controller 123j. The sensing signals of the first thermopile sensor element 121a and the second thermopile sensor element 121b are output to the multiplexer 123a, selected by the multiplexer 123a, amplified by the programmable gain amplifier 123b, and fed to the multiplexer 123c. The sensing signal of the silicon based temperature sensor 122 on the same thermopile sensor chip 12 is output to the buffer amplifier 123d, amplified by the buffer amplifier 123d, and fed to the multiplexer 123c.

Following the above description, the multiplexer 123c selects the sensing signals of the first thermopile sensor element 121a and the second thermopile sensor element 121b or the sense signal of the silicon based temperature sensor 122 to the analog to digital converter 123e, converted into a digital signal by the analog to digital converter 123e, processed by the digital filter 123f, and then the result is stored in the register 123g. In one embodiment, the analog to digital converter 123e may be a Sigma-Delta type analog to digital converter, such as a 16 to 24-bit Sigma-Delta type high precision analog to digital converter. The I²C communication interface 123h communicates with the microcontroller MCU to store or read the data in the register 123g or the non-volatile memory 123i, and select the signal channel and trigger the action of the program controller 123j. The circuit design of the above signal processor 123 is well known to those skilled in the art, and therefore will not be described herein.

According to the above structure, the first thermopile sensor element of the thermopile sensor chip senses the external infrared thermal radiation through the first window of the cap, and the second thermopile sensor element senses the internal infrared thermal radiation of the shielding portion (ie, the package structure) as a basis for correcting compensation, and then the thermal gradient effect of the cap can be compensated. Therefore, the thermal sensor package for earbuds of the present invention can quickly correct the measurement error caused by the package structure to improve the measurement accuracy.

In addition, power management of wireless earbuds is an important issue. In order to save energy, the earbuds may be incorporated with a proximity sensor to determine whether the earbuds is inserted into the ear canal of user or not. A conventional proximity sensor adopts a near infrared light emitter and a photodiode sensor to detect the near infrared reflection light from the user ear. However, the near infrared proximity sensor will be miss activated when any object is close to it. Meanwhile, the optical proximity sensor is power consuming for the wireless earbuds. In one embodiment, the thermal sensor package for earbuds of the present invention can be act as a proximity sensor for power saving. For example, an earbuds with the thermal sensor package of the present invention includes an accelerator sensor. When moving the earbuds, such as housing or wearing the earbuds, the thermal sensor of the present invention will be activated by the accelerator sensor to perform temperature measurements. When the sensing temperature is between 32 degrees Celsius and 38 degrees Celsius, it can be determined that the earbuds is inserted into the ear canal of user and then the signal processor 123 outputs an active signal to notify a start operation of the earbuds. Comparing with the conventional optical proximity sensor, the thermal sensor package for earbuds of the present invention can greatly reduce the false detection rate.

Figure 5:
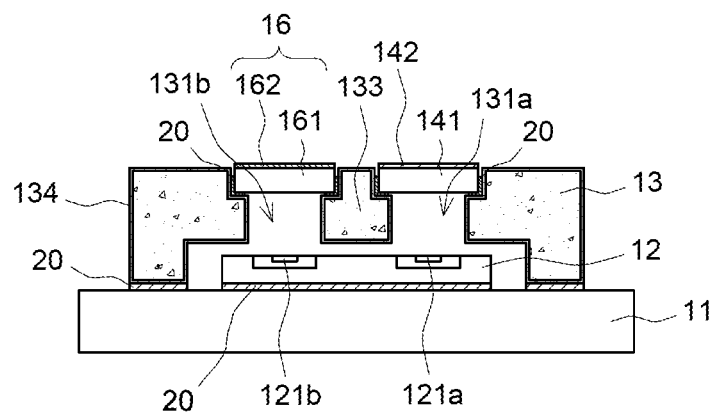
FIG. 5 is a diagram schematically illustrating a thermal sensor package for earbuds according to a second embodiment of the present invention.

In the embodiment shown in FIG. 2, the shielding portion 132 is a part of the cap 13, and preferably includes the metallic layer 134, but is not limited thereto. In one embodiment, referring to FIG. 5, the shielding portion 132 is composed of a shielding element 16. For example, the cap 13 includes a second window 131*b* which is arranged corresponding to the second thermopile sensor element 121*b*. The shielding element 16 is arranged at the second window 131*b* as the shielding portion 132 to shield external infrared thermal radiation. In one embodiment, the shielding element 16 includes a substrate 161 and a shielding layer 162 disposed on a surface of the substrate 161. For example, the shielding layer 162 may be a metallic coating to shield external infrared thermal radiation from the object to be tested. In one embodiment, materials of the substrate 161 of the shielding element 16 and the silicon based infrared lens 141 are the same, such as silicon based material, so that the thermal radiation from the silicon based infrared lens 141 can be compensated. It can be understood that the shielding element 16 is arranged on the cap 13 with thermal conductive adhesive 20. The thermal conductive adhesive 20 can reduce the thermal resistance between the cap 13 and the shielding element 16 so as to make the temperature gradient between the shielding element 16 and the cap 13 is minimized.

Figure 6:
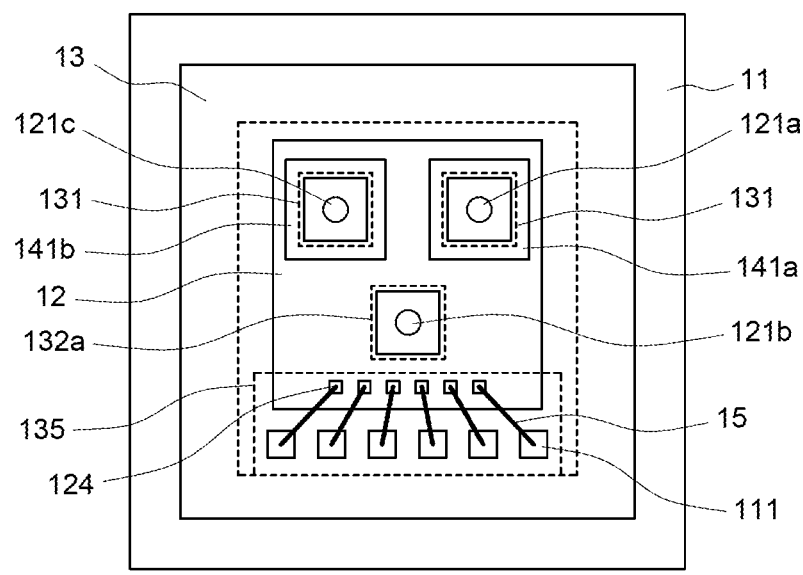
FIG. 6 is a diagram schematically illustrating a thermal sensor package for earbuds according to a third embodiment of the present invention.
Figure 7:
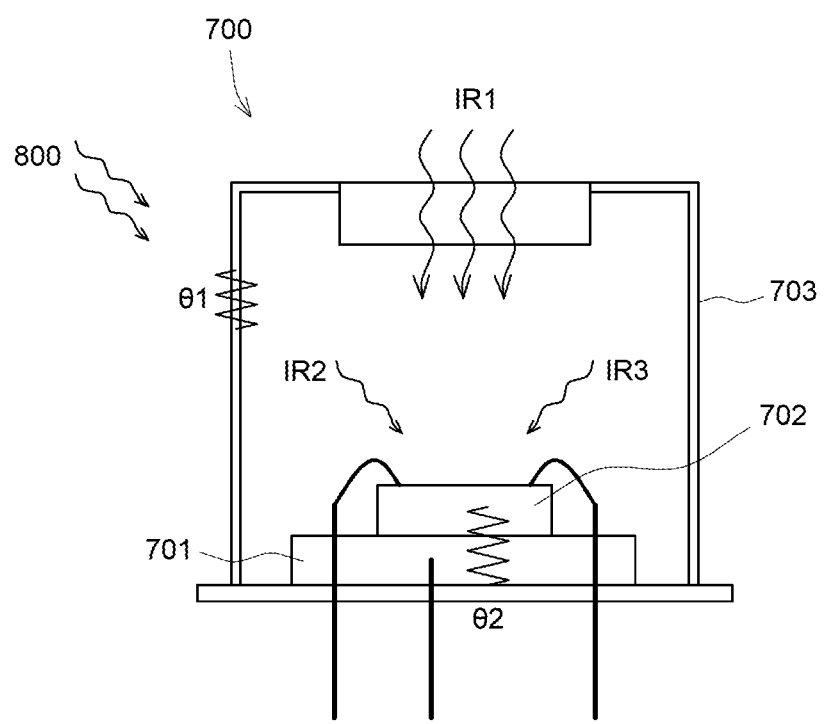
FIG. 7 is a diagram schematically illustrating a thermopile sensor according to a prior art.

Referring to FIG. 6, in one embodiment, the thermopile sensor chip 12 includes a plurality of the first thermopile sensor elements 121*a*, 121*c*, the first windows 131 and the silicon based infrared lenses 141*a*, 141*b* as a thermal sensor with multiple channels. It can be understood that the shielding portion 132 corresponding to the second thermopile sensor element 121*b* may be the part of the cap 13 or the shielding element 16. In one embodiment, the filtering band of the filters coated on the silicon based infrared lenses 141*a*, 141*b* are different, so that the thermal sensor package for earbuds of the present invention can sense different infrared bands.

According to the above structure, the packaging step of the thermal sensor package for earbuds of the present invention can be greatly simplified. For example, the caps 13 can be made and connected with each other by an M×N array shape by injection molding, and then the metallic layers 134 are formed on the inner surface and the outer surface of the caps 13. It can be understood that the caps 13 are connected with each other by partial connection, so that the metallic layers 134 on the inner and the outer surface of the cap 13 are connected which increase the heat conduction effect. Next, the silicon based infrared lenses 141 are cut into an appropriate size and placed at one end of the first window 131 of each cap 13, thus completing the fabrication process of the caps 13. The thermopile sensor chips 12 are respectively mounted on the package substrates 11 by an existing manufacturing method, wherein the package substrates 11 are arranged in M×N array shape, and then the thermopile sensor chips 12 are electrically connected to the corresponding package substrate 11 by the wires 15. Then, the caps 13 are placed on the package substrates 11 and the thermopile sensor chips 12 and wires 15 are covered by the caps 13 to complete the package process. After a singulation process, the SMD package and test process can be performed. According to the above manufacturing process, the thermal sensor package for earbuds of the present invention can be miniature, cost effective and ease of manufacture.

To summarize the foregoing descriptions, the thermal sensor package for earbuds of the present invention is provided with two thermopile sensor elements on a single thermopile sensor chip, and the two thermopile sensor elements are separated by the block wall of the cap. One of the thermopile sensor elements senses the external infrared thermal radiation through the window of the cap, and the other thermopile sensor element senses the internal infrared thermal radiation from the shielding portion (i.e. the package structure) as the basis for correcting compensation, so that the thermal gradient effect of the cap can be compensated. Therefore, the thermal sensor package for earbuds of the present invention can quickly correct the measurement error caused by the package structure to improve the measurement accuracy for long term inside the ear canal of user. In addition, the thermal sensor package for earbuds of the present invention has a simple packaging step and is easy to arrange the silicon based infrared lens to expand its application. Furthermore, the thermal sensor package for earbuds of the present invention can be acted as a proximity sensor, so that the earbuds with the thermal sensor package for earbuds of the present invention might eliminate the optical proximity sensor of prior art and offer power saving for longer battery operation.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. A thermal sensor package for earbuds comprising:
   a package substrate;
   a thermopile sensor chip mounted on the package substrate and electrically connected with the package substrate, wherein the thermopile sensor chip comprises:
   a first thermopile sensor element for receiving external infrared thermal radiation to generate a first sensing signal;
   a second thermopile sensor element for receiving internal infrared thermal radiation to generate a second sensing signal;
   a silicon based temperature sensor for sensing ambient temperature to generate an ambient temperature signal; and
   a signal processor electrically connected with the first thermopile sensor element, the second thermopile sensor element and the silicon based temperature sensor for processing the first sensing signal, the second sensing signal and the ambient temperature signal to output a sensing temperature of the thermopile sensor chip;
   a cap arranged on the package substrate to define an accommodation space with the package substrate to accommodate the thermopile sensor chip and including a first window, a shielding portion and a block wall, wherein the first window is arranged corresponding to the first thermopile sensor element, the shielding portion is arranged corresponding to the second thermopile sensor element so that the second thermopile sensor element receives the internal infrared thermal radiation from the shielding portion, and the block wall is arranged between the first thermopile sensor element and the second thermopile sensor element; and a silicon based infrared lens arranged at the first window of the cap to limit a field of view of the first thermopile sensor element.

2. The thermal sensor package for earbuds according to claim 1, wherein the silicon based infrared lens is Fresnel lens.

3. The thermal sensor package for earbuds according to claim 1, wherein the silicon based infrared lens is coated with a filter.

4. The thermal sensor package for earbuds according to claim 1, wherein a material of the cap is liquid crystal polymer (LCP).

5. The thermal sensor package for earbuds according to claim 1, wherein the cap is coated with a metallic layer on an inner surface and an outer surface.

6. The thermal sensor package for earbuds according to claim 1, wherein the metallic layer comprises at least one of copper, aluminum, nickel, chrome and stainless steel.

7. The thermal sensor package for earbuds according to claim 1, wherein the cap includes a second window corresponding to the second thermopile sensor element and a shielding element arranged at the second window as the shielding portion.

8. The thermal sensor package for earbuds according to claim 7, wherein the shielding element is made of silicon material with metallic coating.

9. The thermal sensor package for earbuds according to claim 7, wherein the shielding element is arranged at the second window of the cap with thermal conductive adhesive.

10. The thermal sensor package for earbuds according to claim 1, wherein the silicon based infrared lens is arranged at the first window of the cap with thermal conductive adhesive.

11. The thermal sensor package for earbuds according to claim 1, wherein the cap is attached to the package substrate with thermal conductive adhesive.

12. The thermal sensor package for earbuds according to claim 1, wherein a distance between the block wall of the cap and the thermopile sensor chip is equal to or less than 100 µm.

13. The thermal sensor package for earbuds according to claim 1, wherein a distance between the block wall of the cap and the thermopile sensor chip is greater than 25 µm and less than 75 µm.

14. The thermal sensor package for earbuds according to claim 1, wherein a distance between the shielding portion and the second thermopile sensor element is equal to or greater than 100 µm.

15. The thermal sensor package for earbuds according to claim 1, wherein a distance between the shielding portion and the second thermopile sensor element is between 200 µm and 500 µm.

16. The thermal sensor package for earbuds according to claim 1, wherein a material of the package substrate is bismaleimide triazine (BT) resin or ceramic material.

17. The thermal sensor package for earbuds according to claim 1, wherein the signal processor further output an active signal when the sensing temperature is between 32 degrees Celsius and 38 degrees Celsius.

* * * * *